United States Patent
Wang et al.

(10) Patent No.: US 8,664,368 B2
(45) Date of Patent: Mar. 4, 2014

(54) FULLY HUMAN MONOCLONAL ANTIBODY TO VEGF, PREPARATION METHOD AND USE THEREOF

(75) Inventors: Shuhui Wang, Shanghai (CN); Chuan Li, Shanghai (CN); Ying Kan, Shanghai (CN); Xin Tong, Shanghai (CN)

(73) Assignee: Shanghai Biomabs Pharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 13/579,218

(22) PCT Filed: Apr. 16, 2010

(86) PCT No.: PCT/CN2010/000513
§ 371 (c)(1),
(2), (4) Date: Sep. 17, 2012

(87) PCT Pub. No.: WO2011/103702
PCT Pub. Date: Sep. 1, 2011

(65) Prior Publication Data
US 2013/0046081 A1   Feb. 21, 2013

(30) Foreign Application Priority Data
Feb. 25, 2010   (CN) .......................... 2010 1 0125263

(51) Int. Cl.
*C07K 16/22* (2006.01)
*C07K 16/18* (2006.01)
*C07K 14/475* (2006.01)
*A61K 39/395* (2006.01)

(52) U.S. Cl.
USPC ................ 530/388.1; 530/388.24; 424/141.1; 424/145.1; 424/158.1

(58) Field of Classification Search
None
See application file for complete search history.

(56) References Cited

FOREIGN PATENT DOCUMENTS

| | | |
|---|---|---|
| CN | 1445242 | 10/2003 |
| CN | 1946422 | 4/2007 |
| CN | 101148474 | 3/2008 |

OTHER PUBLICATIONS

Tian, X. J. et al. "Construction of human antibody library and analysis of its diversity"; Chin. J. Biochem, Mol. Biol. 16(2):200-205 (2000).

*Primary Examiner* — Phuong Huynh
(74) *Attorney, Agent, or Firm* — Cesari and McKenna, LLP

(57) ABSTRACT

The present invention provides a fully human anti-VEGF monoclonal antibody, the preparation method and use thereof. The fully human anti-VEGF monoclonal antibody is obtained by using antibody phage display technology, which has higher antibody affinity and stronger capacity for inhibiting tumor cell proliferation in comparison with humanized antibody bevacizumab, and can be used to prepare anti-tumor medicines.

6 Claims, 1 Drawing Sheet

FULLY HUMAN MONOCLONAL ANTIBODY TO VEGF, PREPARATION METHOD AND USE THEREOF

CROSS REFERENCE TO RELATED APPLICATIONS

This application is a National Stage of International Application No. PCT/CN2010/000513, filed on Apr. 16, 2010, which claims priority to Chinese Patent Application No. 201010125263.7, filed Feb. 25, 2010. The contents of the prior applications are incorporated herein by reference in their entirety.

FIELD OF THE INVENTION

The present invention relates to the field of biotechnology. In particular, the present invention relates to a fully human monoclonal antibody, the preparation method and use thereof.

BACKGROUND OF THE INVENTION

Tumor, particularly malignant tumor is a disease which causes serious harm to the health of human bodies and is the second leading cause of death among all diseases in the world today. The incidence tendency of malignant tumor is rising obviously in recent years. However, the treatment effect is limited, with high metastasis rate in advanced stage and poor prognosis. Although, conventional treatments currently used in clinical such as radiotherapy, chemotherapy and surgical treatment can ease the pain to a large extent and prolong the life span, there are still many limitations of these therapies and it's difficult to improve the treatment effect further.

There are two distinct phases of tumor growth, namely from the avascular phase of slow growth to the vascular phase of rapid proliferation. Angiogenesis enables the tumors to obtain adequate nutrition and therefore complete the angiogenic switch. If there is no angiogenesis, the primary tumor will not grow to exceed 1-2 mm and tumor metastasis will not be realized. Vascular endothelial growth factor (VEGF) is a kind of growth factor which can promote endothelial cell differentiation and proliferation, promote new blood vessel formation and increase vascular permeability. It binds to vascular endothelial growth factor receptor on the surface of cells, and functions by activating tyrosine kinase signal transduction pathways. In tumor tissues, the tumor cells, invasive tumor macrophages and mast cells can secrete high levels of VEGF, stimulate the tumor vascular endothelial cells in the form of paracrine secretion, promote the proliferation and migration of endothelial cells, induce angiogenesis, promote the sustainable growth of tumor and increase vascular permeability, cause fibrin calm of the surrounding tissues, promote the invasion of monocytes, fibroblast cells and endothelial cells, facilitate the formation of tumor stroma and the entries of tumor cells into new vessels and promote tumor metastasis. Thus, the inhibition of tumor angiogenesis is considered to be one of the most promising treatments of tumors.

Bevacizumab (Avastin) is a humanized anti-human VEGF antibody (Cancer Res 1997; 57: 4593-9). It was approved as a first-line drug for the treatment of metastatic colorectal cancer by the U.S. Food and Drug Administration in 2004. However, bevacizumab is a humanized antibody that retains murine CDR regions and a few murine residues of FR regions. It is still not a fully humanized antibody and still has a problem of low affinity.

SUMMARY OF THE INVENTION

The present invention constructs a large-capacity human natural phage antibody library and obtains a fully human anti-VEGF antibody 11A7 by selecting therefrom.

More particularly, the present invention provides a fully human anti-VEGF antibody, having an amino acid sequence of heavy chain variable region as shown in SEQ ID NO: 6, and an amino acid sequence of light chain variable region as shown in SEQ ID NO: 8.

The above fully human anti-VEGF antibody according to the present invention has an amino acid sequence of heavy chain as shown in SEQ ID NO: 10, and an amino acid sequence of light chain as shown in SEQ ID NO: 12.

The present invention also provides an isolated nucleotide encoding the above fully human anti-VEGF antibody.

The above nucleotide according to the present invention has a nucleotide sequence encoding heavy chain variable region of the fully human anti-VEGF antibody as shown in SEQ ID NO: 5, and a nucleotide sequence encoding light chain variable region of the fully human anti-VEGF antibody as shown in SEQ ID NO: 7.

The above nucleotide according to the present invention has a nucleotide sequence encoding heavy chain of the fully human anti-VEGF antibody as shown in SEQ ID NO: 9, and a nucleotide sequence encoding light chain of the fully human anti-VEGF antibody as shown in SEQ ID NO: 11.

The present invention also provides an expression vector containing the above nucleotide, which is pcDNA3.1/ZEO (+) or pcDNA3.1 (+).

The present invention also provides a host cell transfected with the above expression vector, which is CHO-K1 cell.

The present invention further provides a method for preparing the above fully human antibody, comprising selecting human phage antibody library to obtain a fully human anti-VEGF single-chain antibody with high affinity; constructing an eukaryotic expression vector of the complete molecular of the fully human anti-VEGF antibody; expressing the complete molecular of fully human anti-VEGF antibody in CHO cells; and purifying the complete molecular of the fully human anti-VEGF antibody.

The present invention also provides a use of the above fully human anti-VEGF antibody in preparing medicines for treatment of tumors, wherein said tumor is colorectal cancer.

The obtained antibody are used to perform a series of experiments in the present invention and the experiment results show that compared to humanized antibody bevacizumab and human anti-VEGF antibody 6A6 (which is prepared according to the method disclosed in Chinese Patent Application No. 02111093.X entitled "Humanized Anti-vascular Endothelial Growth Factor Monoclonal Antibody, Preparation Method and Pharmaceutical Composition Thereof" filed on Mar. 20, 2002, the antibody obtained according to the present invention has higher antibody affinity and stronger inhibition effect on tumor cell proliferation; and the results of antitumor experiment in vivo show that the antibody of the present invention can inhibit tumor growth significantly.

DETAILED DESCRIPTION OF THE INVENTION

Figure 1:
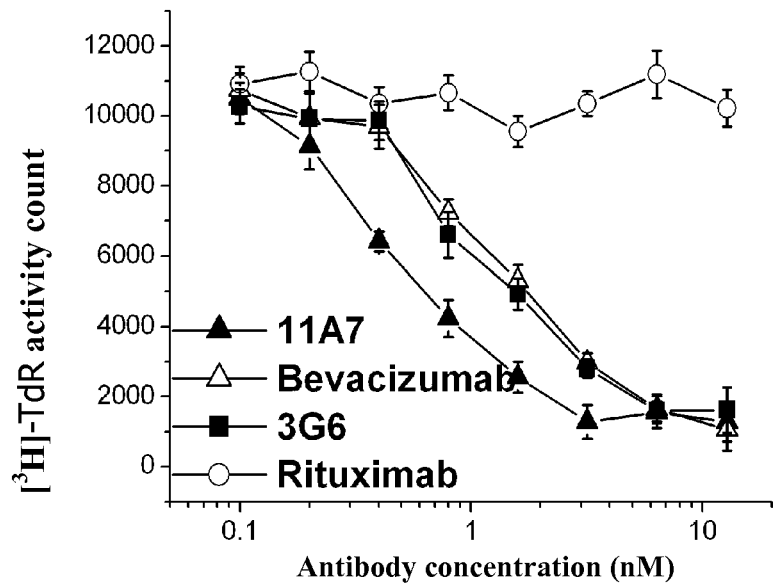
FIG. 1 shows the results of cell proliferation assay.

The following examples and experiment examples are used to further illustrate the present invention only and should not be construed to limit the present invention.

(1) Cloning of Genes Encoding Human Antibody Light and Heavy Chain Constant Region Healthy human lymphoma cells were isolated with lymphocyte separation medium (Dingguo Biotechnology Development Company, China) and total RNA was extracted using Trizol reagent (Invitrogen). The genes encoding antibody heavy and light chain constant region were amplified by RT-PCR reaction, with the primers designed according to the sequences reported in the reference (Cell, 1980, 22: 197-207) and reference (Nucleic Acids Research, 1982, 10: 4071-4079), respectively. The PCR products were purified by agarose gel electrophoresis and recovered and cloned into pGEM-T vectors (Promega). Correct clones were obtained by sequencing verification. SEQ ID NO: 1 and SEQ ID NO: 2 showed the nucleotide sequence and amino acid sequence of the heavy chain constant region ($C_H$), respectively. SEQ ID NO: 3 and SEQ ID NO: 4 showed the nucleotide sequence and amino acid sequence of the light chain constant region ($C_L$), respectively. In this example, the correct clones were designated as pGEM-T/$C_H$ and pGEM-T/$C_L$.

(2) Preparation of cDNA 20 ml of peripheral blood was collected from each of 50 healthy people and mononuclearcells were isolated with lymphocyte separation medium (Tianjin blood research Institute of Medical Science). Total cellular RNA was extracted from the isolated human peripheral blood lymphocytes using Trizol reagent (Invitrogen). cDNA was reverse transcribed using cDNA reverse transcription kit (Shanghai Biocolor Biotechnolgy Ltd.). The above procedures were performed according to the manufacturer's instructions.

(3) Design of Primers $V_H$Back, $V_H$For, $V_L$Back and $V_L$For, the primers for cloning genes of human antibody heavy chain variable region ($V_H$) and light chain variable region ($V_L$), were designed and synthesized according to the reference (Immunotechnology, 1998, 3:271-278). Sequences of $V_H$Back, $V_H$For, $V_L$Back and $V_L$For were shown in Immunotechnology, 1998, 3:271-278. Wherein, $V_H$Back primer was added with an Sfi I site-containing sequence: atg gcc cag ccg gcc atg gcc (SEQ ID NO: 13) at the 5' end; $V_H$For primer was added with a sequence: gcc aga acc acc gcc gcc gga gcc acc acc gcc ESEQ ID NO:14) at the 5' end; $V_L$Back primer was added with a sequence: tcc ggc ggc ggt ggt tct ggc gga ggc gga tct (SEQ ID NO:15) at the 5' end; and $V_L$For primer was added with a Not I site-containing sequence: atg cgg ccg c (SEQ ID NO:16) at the 5' end.

(4) Construction and Selection of Phage Antibody Library

Phage single-chain antibody library was constructed with the cDNA of (2) and the primers of (3) using recombinant Phage antibody system kit (Amersham Biosciences) and then selected with a specific antigen. The methods of constructing and selecting the antibody library were performed according to the instructions of recombinant Phage antibody system kit. The specific antigen "Recombinant Human VEGF165 Protein" was purchased from R&D.

A anti-human VEGF single-chain antibody 11A7ScFv was obtained after several times of selection, and its gene sequence was obtained by sequencing. SEQ ID NO: 5 and SEQ ID NO: 6 show the nucleotide sequence and amino acid sequence of the heavy chain variable region (VH) of 11A7ScFv, respectively. SEQ ID NO: 7 and SEQ ID NO: 8 show the nucleotide sequence and amino acid sequence of the light chain variable region ($V_L$) of 11A7ScFv, respectively.

(5) Expression of Fully Human Antibody in Eukaryotic Cells

3E12ScFv genes and pGEM-T/$C_H$ vectors were used as template to synthesize fully human antibody heavy chain genes by overlapping PCR. The reaction conditions were: 95° C. for 15 min; 94° C. for 50 sec, 58° C. for 50 sec, 72° C. for 50 sec, for 30 cycles; 72° C. for 10 min Besides, the fully human antibody heavy chain genes were allowed to contain HindIII restriction enzyme sites and a signal peptide gene sequence at the 5' end and contain translation stop codons TAA and EcoRI restriction enzyme sites at the 3' end. The sequence encoding the signal peptide was: (ATG-GATTTTCAGGTGCAGATTTTCAGCTTC-CTGCTAATCAGTGCCTCAGTCAT AATATCCA-GAGGA)(SEQ ID NO:17). Finally, PCR amplification products were separated by agarose gel electrophoresis and the band of interest was recovered and cloned into pGEM-T vectors (Promega) to select and sequence positive clones. Clones with the correct sequence were selected and digested with Hind III and EcoRI, and the fully human antibody heavy chain fragments 3E12$V_H C_H$ were purified and recovered by agarose gel electrophoresis and ligated into the HindIII and EcoRI-digested plasmids pcDNA3.1(+) (Invitrogen) to construct fully human heavy chain eukaryotic expression vectors pcDNA3.1(+) (3E12$V_H C_H$).

3E12ScFv genes and pGEM-T/$C_L$ vectors were used as template to synthesize fully human antibody light chain genes by overlapping PCR. The reaction conditions were: 95° C. for 15 min; 94° C. for 50 sec, 58° C. for 50 sec, 72° C. for 50 sec, for 30 cycles; 72° C. for 10 min. The obtained PCR products contained HindIII restriction enzyme sites and a signal peptide gene sequence at the 5' end and contained translation stop codons TAA and EcoRI restriction enzyme sites at the 3' end. The sequence encoding the signal peptide was: (ATG-GATTTTCAGGTGCAGATTTTCAGCTTC-CTGCTAATCAGTGCCTCAGTCAT AATATCCA-GAGGA)(SEQ ID NO:17). Clones with the correct sequences were selected and digested with Hind III and EcoRI, and the fully human antibody light chain fragments 3E12$V_L C_L$ were purified and recovered by agarose gel electrophoresis and ligated into the HindIII and EcoRI-digested plasmids pcDNA3.1/ZEO(+) (Invitrogen) to construct fully human light chain eukaryotic expression vectors pcDNA3.1/ZEO(+) (3E12$V_L C_L$).

$3 \times 10^5$ CHO-K1 cells (ATCC CRL-9618) were inoculated into 3.5cm tissue culture dishes, and transfected when the cells were cultured to 90-95% confluence: 10 μg of plasmids (4 μg of plasmids pcDNA3.1(+) (11A7$V_H C_H$), 6 μg of plasmids pcDNA3.1/ZEO(+) (11A7$V_L C_L$)) and 20 μl of Lipofectamine2000 Reagent (Invitrogen) were taken to perform transfection according to the instructions of Lipofectamine2000 Reagent kit. After transfection for 24 hours, the cells were transferred to DMEM medium containing 600 μg/ml G418 (Invitrogen) and 250 μg/ml Zeocin (Invitrogen) to select resistant clones. Cell culture supernatants were taken to select high-expressing clones by ELISA: ELISA plates were coated with goat anti-human IgG (Fc) overnight at 4° C. and blocked with 2% BSA-PBS at 37° C. for 2h; the culture supernatants of resistant clones to be tested or standard sample (Human myeloma IgG1, κ) (Sigma) were added and warm incubated at 37° C. for 2 h; HRP-goat anti-human IgG (κ) (Southern Biotechnology Associates) was added and warm incubated at 37° C. for 1 h for combining reaction, and chromogenic reagent TMB was added and reacted at 37° C. for 5 min, finally $H_2SO_4$ was used to stop the reaction and $A_{450}$ value was measured. The high-expressing clones obtained by selection were enlarged cultured in serum-free medium, and fully human antibodies 11A7 were isolated and purified by Protein A affinity column (GE). The purified antibodies were dialyzed against PBS and finally quantified by UV absorbance. SEQ ID NO: 9 and SEQ ID NO: 10 show the nucleotide sequence and amino acid sequence of the heavy chain of fully human antibody 11A7, respectively. SEQ ID NO: 11 and SEQ ID NO: 12 show the nucleotide sequence and amino acid sequence of the light chain of fully human antibody 11A7, respectively.

EXPERIMENT EXAMPLES

Human anti-VEGF antibody 6A6 was prepared according to the method disclosed in Chinese Patent Application No. 02111093.X entitled "Humanized Anti-vascular Endothelial Growth Factor Monoclonal Antibody, Preparation Method and Pharmaceutical Composition Thereof" filed on Mar. 20, 2002.

Experiment Example 1

Affinity Detection of VEGF Antibody

Affinity constant of VEGF antibody was detected using Biacore T100 system (Biacore AB, Uppsala, Sweden). VEGF165 (R&D) was covalently linked to CM5 biological sensor chips (Biacore) by amino-coupling. Fully human antibody 11A7, Bevacizumab, human antibody 6A6 (prepared according to the method disclosed in Chinese Patent Application No. 02111093.X entitled "Humanized Anti-vascular Endothelial Growth Factor Monoclonal Antibody, Preparation Method and Pharmaceutical Composition Thereof" filed on Mar. 20, 2002) and negative control antibody (Rituximab, commercial available) were formulated with PBS/0.05% TWEEN-20 (ICI Americas) (an eradicator) into solutions with different concentrations (2-fold dilution)) and passed through the chips at a flow rate of 50 μl/min. After each examination, they were washed with 5 μl of 50 mM hydrochloric acid aqueous solution at a flow rate of 3 μl/min so as to wash away the residual antibodies from the immobilized ligands. The binding curves were subjected to nonlinear regression analysis using BIAevalution software (T100 evalution version 2.0, Biacore). The results are shown in table 1. The KD value of fully human antibody 11A7 was significantly lower than that of Bevacizumab and fully human antibody 6A6, demonstrating that the affinity of fully human antibody 11A7 to VEGF was higher than that of Bevacizumab and fully human antibody 6A6. The results of affinity experiment are shown in Table 1.

TABLE 1

Results of affinity experiment

| Antibody | $K_{on}$ ($M^{-1}S^{-1}/10^4$) | $K_{off}$ ($10^4 S^{-1}$) | $K_D$ (nM) |
| --- | --- | --- | --- |
| 11A7 | 8.24 | 0.71 | 0.86 |
| Bevacizumab | 5.12 | 1.03 | 2.01 |
| 6A6 | 4.19 | 0.95 | 2.27 |
| Rituximab | ND | ND | ND |

Experiment Example 2

Experiment of Inhibition of HUVEC Cells Proliferation by VEGF Antibody

Experiment steps: The well-growing HUVEC cells (Cascade Biologics) were adjusted to a cell density of $2.5 \times 10^4$/ml, inoculated into 96 cell culture plates with 200 μl/well and cultured in a 5% $CO_2$ incubator at 37° C. for 24 h and then cultured in serum-free medium for another 72 h, added with VEGF antibody of different concentrations and incubated at 37° C. for 1 h, with anti-CD20 antibody Rituximab as negative control and three parallel wells for each concentration; added with VEGF 165 (R&D) until reaching a final concentration of 25 ng/ml and cultured for another 24 h; then added with 10 μl of [$^3$H]-TdR(18.5 kBq/well) and incubated in a incubator at 37° C. for 7 h. The cells were collected onto a glass fiber filtration film with cell collector and counted with [$^3$H] liquid scintillation counter. The results are shown as FIG. 1.

The results showed that the negative control antibody (Rituximab) cannot effectively inhibit VEGF-induced HUVEC proliferation, however, all of fully human antibody11A7, Bevacizumab and human antibody 6A6 can effectively inhibit VEGF-induced HUVEC proliferation. The activity of inhibiting VEGF-induced HUVEC proliferation of fully human antibody 11A7 was significantly stronger than that of Bevacizumab and human antibody 6A6 ($P<0.05$, t-test, the concentration range of the antibodies was 0.4-3.2 nM).

Experiment Example 3

In vivo Tumor Growth Inhibition Eexperiment of VEGF Antibody

Figure 2:
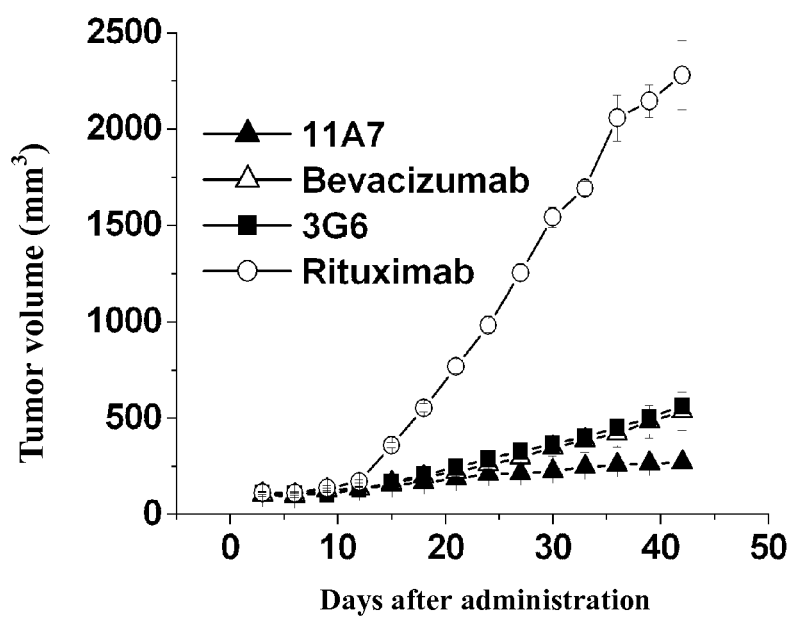
FIG. 2 shows the curve of tumor growth.

Experiment steps: In order to detect the activity of inhibiting tumor growth of the VEGF antibodies in vivo, first LM3 cells (Human hepatoma cells, from Liver Cancer Institute, Medical College of the Fudan University, Shanghai, China) were inoculated into the right axillary lateral subcutaneous of female mice with severe immune deficient (from the Animal Experiment Center of the Second Military Medical University, China). Each mouse was administrated with 25 mg/kg of VEGF antibody and unrelated control protein Rituximab on the same day and then subjected to subcutaneous injection every other day for 4 weeks. After six weeks, the length and width of the tumors were measured to calculate the volume of the tumors every 3 days. The results are shown in FIG. 2.

The results showed that the negative control antibody (Rituximab) cannot inhibit tumor growth effectively, however, all of fully human antibody 11A7, Bevacizumab and human antibody 6A6 can inhibit tumor growth effectively. And from the 18$^{th}$ day, the activity of inhibiting tumor growth of fully human antibody 11A7 was stronger than that of Bevacizumab and human antibody 6A6, with significant difference ($P<0.05$, Mann-Whitney test, when observation time is longer than 35 days).

What is claimed is:

1. A fully human anti-VEGF monoclonal antibody, having an amino acid sequence of heavy chain variable region as shown in SEQ ID NO: 6 and an amino acid sequence of light chain variable region as shown in SEQ ID NO: 8.

2. The fully human anti-VEGF monoclonal antibody of claim 1, having an amino acid sequence of heavy chain as shown in SEQ ID NO: 10 and an amino acid sequence of light chain as shown in SEQ ID NO: 12.

3. A method of treating a tumor in a subject, the method comprising administering to the subject in need thereof the fully human anti-VEGF monoclonal antibody of claim 1.

4. The method of claim 3, wherein the tumor is colorectal cancer.

5. A method of treating a tumor in a subject, the method comprising administering to the subject in need thereof the fully human anti-VEGF monoclonal antibody of claim 2.

6. The method of claim 5, wherein the tumor is colorectal cancer.

* * * * *

SEQUENCE LISTING

<160> NUMBER OF SEQ ID NOS: 17

<210> SEQ ID NO 1
<211> LENGTH: 990
<212> TYPE: DNA
<213> ORGANISM: Artificial sequence -continued
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody heavy
      chain constant region (CH)

<400> SEQUENCE: 1

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggaaga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 2
<211> LENGTH: 330
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody heavy
      chain constant region (CH)

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 318
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody light
      chain constant region (CL)

<400> SEQUENCE: 3
actgtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgt                                                  318

<210> SEQ ID NO 4
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody light
      chain constant region (CL)

<400> SEQUENCE: 4

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65              70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 5
<211> LENGTH: 369
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of heavy chain variable
      region of fully human antibody 11A7

<400> SEQUENCE: 5

```
caggtgcagc tggtgcagtc tggggctgag gtgaagaagc ctggggcctc agtgaaggtc     60
tcctgcaagg cttctggata caccttcacc agttatgata tcaactgggt gcgacaggcc    120
actggacaag gcttgagtg gatgggatgg atgaaccctaacagtggtaa cacaggctat     180 gcacagaagt tccagggcag agtcaccatg accaggaaca cctccataag cacagcctac    240
atggagctga gcagcctgag atctgaggac acggccgtgt attactgtgc gagaggtggg    300
tatagcagca gctggtacta ctggtacttc gatctctggg gccgtggcac cctggtcact    360
gtctcctca                                                             369
```

<210> SEQ ID NO 6
<211> LENGTH: 123
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain variable
      region of fully human antibody 11A7

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65              70                  75                  80

Met Glu Leu Ser Ser Leu Arg Ser Glu Asp Thr Ala Val Tyr Tyr Cys
                85                  90                  95
```

Ala Arg Gly Gly Tyr Ser Ser Ser Trp Tyr Tyr Trp Tyr Phe Asp Leu
            100                 105                 110

Trp Gly Arg Gly Thr Leu Val Thr Val Ser Ser
        115                 120

<210> SEQ ID NO 7
<211> LENGTH: 330
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain variable
      region of fully human antibody 11A7

<400> SEQUENCE: 7
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcctgt gtacactttt   300
ggccagggga ccaagctgga gatcaaacgt                                    330

<210> SEQ ID NO 8
<211> LENGTH: 110
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain variable
      region of fully human antibody 11A7

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Val Tyr Thr Phe Gly Gln Gly Thr Lys Leu Glu Ile Lys Arg
            100                 105                 110

<210> SEQ ID NO 9
<211> LENGTH: 1359
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of heavy chain of fully
      human antibody 11A7

<400> SEQUENCE: 9

```
caggtgcagc tggtgcagtc tgggctgag gtgaagaagc ctggggcctc agtgaaggtc     60
tcctgcaagg cttctggata caccttcacc agttatgata tcaactgggt gcgacaggcc    120
actggacaag gcttgagtg gatgggatgg atgaaccccta acagtggtaa cacaggctat    180
gcacagaagt tccagggcag agtcaccatg accaggaaca cctccataag cacagcctac    240
atggagctga gcagcctgag atctgaggac acggccgtgt attactgtgc gagaggtggg    300
tatagcagca gctggtacta ctggtacttc gatctctggg gccgtggcac cctggtcact    360
gtctcctcag ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gccccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtcc ccgggtaaa                          1359
```

<210> SEQ ID NO 10
<211> LENGTH: 453
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain of fully human antibody 11A7

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Gly Tyr Ser Ser Ser Trp Tyr Tyr Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 11
<211> LENGTH: 648
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain of fully
      human antibody 11A7

```
<400> SEQUENCE: 11
gacatccaga tgacccagtc tccatcctcc ctgtctgcat ctgtaggaga cagagtcacc        60
atcacttgcc gggcaagtca gggcattaga aatgatttag ctggtatcag cagaaaacca       120
gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag cataatagtt accctcctgt gtacactttt       300
ggccagggga ccaagctgga gatcaaacgt actgtggctg caccatctgt cttcatcttc       360
ccgccatctg atgagcagtt gaaatctgga actgcctctg ttgtgtgcct gctgaataac       420
ttctatccca gagaggccaa agtacagtgg aaggtggata acgccctcca atcgggtaac       480
tcccaggaga gtgtcacaga gcaggacagc aaggacagca cctacagcct cagcagcacc       540
ctgacgctga gcaaagcaga ctacgagaaa cacaaagtct acgcctgcga agtcacccat       600
cagggcctga gctcgcccgt cacaaagagc ttcaacaggg gagagtgt                    648

<210> SEQ ID NO 12
<211> LENGTH: 216
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain of fully
      human antibody 11A7

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Val Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

```
<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
atggcccagc cggccatggc c                                             21

<210> SEQ ID NO 14
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 14
gccagaacca ccgccgccgg agccaccacc gcc                                33

<210> SEQ ID NO 15
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15
tccggcggcg gtggttctgg cggaggcgga tct                                33

<210> SEQ ID NO 16
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 16
atgcggccgc                                                          10

<210> SEQ ID NO 17
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 17
atggattttc aggtgcagat tttcagcttc ctgctaatca gtgcctcagt cataatatcc   60
agagga                                                              66
```